(12) United States Patent
Coats

(10) Patent No.: US 9,854,811 B2
(45) Date of Patent: Jan. 2, 2018

(54) TREATMENT OF PLANTS, FRUITS AND VEGETABLES TO INCREASE GROWTH, ELIMINATE INSECTS AND INCREASE SHELF-LIFE WITH ALOE VERA GEL

(71) Applicant: Coats Agri Aloe, LLC, Dallas, TX (US)

(72) Inventor: Billy C. Coats, Garland, TX (US)

(73) Assignee: Coats Agri Aloe, LLC, Plano, TX (US)

( * ) Notice: Subject to any disclaimer, the term of this patent is extended or adjusted under 35 U.S.C. 154(b) by 559 days.

(21) Appl. No.: 13/718,845

(22) Filed: Dec. 18, 2012

(65) Prior Publication Data
US 2013/0102466 A1    Apr. 25, 2013

Related U.S. Application Data

(63) Continuation of application No. 11/941,777, filed on Nov. 16, 2007, now Pat. No. 8,367,624.

(60) Provisional application No. 60/859,336, filed on Nov. 16, 2006.

(51) Int. Cl.
| | |
|---|---|
| A01N 65/42 | (2009.01) |
| A01N 3/00 | (2006.01) |
| A01N 65/00 | (2009.01) |
| A23B 7/154 | (2006.01) |
| A23B 7/16 | (2006.01) |

(52) U.S. Cl.
CPC .............. *A01N 65/42* (2013.01); *A01N 3/00* (2013.01); *A01N 65/00* (2013.01); *A23B 7/154* (2013.01); *A23B 7/16* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,039,470 A | 8/1977 | Kalmar | |
| 4,602,004 A * | 7/1986 | Cohen | A01N 35/06 514/23 |
| 4,680,889 A | 7/1987 | Carlson | |
| 4,783,342 A | 11/1988 | Polovina | |
| 4,946,694 A | 8/1990 | Gunnerson et al. | |
| 4,966,892 A | 10/1990 | McAnalley | |
| 5,356,811 A * | 10/1994 | Coats | 435/267 |
| 5,922,774 A | 7/1999 | Winslow | |
| 6,482,942 B1 * | 11/2002 | Vittori | A23L 33/22 536/127 |
| 8,367,624 B2 | 2/2013 | Coats | |
| 9,622,488 B2 | 4/2017 | Coats | |
| 2004/0156920 A1 | 8/2004 | Kane | |
| 2004/0197364 A1 | 10/2004 | Brown | |
| 2006/0182775 A1 * | 8/2006 | Everett | A01N 65/00 424/405 |
| 2010/0154498 A1 * | 6/2010 | Valencia | C05D 9/02 71/23 |

FOREIGN PATENT DOCUMENTS

| | | |
|---|---|---|
| AU | 2007319150 | 11/2012 |
| CN | 102960160 A | 3/2013 |
| ES | 2234431 A * | 6/2005 |
| ES | 2234431 A1 | 6/2005 |
| JP | 59108702 A | 12/1982 |
| JP | 19840259642 A * | 12/1984 |
| JP | 61136583 A | 6/1986 |
| WO | 2008061235 A2 | 5/2008 |
| WO | 2017024252 A1 | 2/2017 |

OTHER PUBLICATIONS

Translation of JPS61136583.*
"Aloe vera coating may prolong freshness, safety of fruits and vegetables," BrightSurf.com, accessed Feb. 7, 2006 at http://www.brightsurf.com/news/headlines/view.article.php?ArticleID=21057.
Extended European Search Report prepared by the European Patent Office for EP 07864543.9 dated Aug. 30, 2012, 12 pages.
International Search Report and Written Opinion prepared by the Australian Patent Office for PCT/US2007/084998 dated Apr. 23, 2008, 10 pages.
Martinez-Romero, et al., "Postharvest Sweet Cherry Quality and Safety Maintenance by Aloe Vera Treatment: A New Edible Coating," Postharvest Biology and Technology (2006), 39:93-100.
Valverde et al., "Novel Edible Coating Based on Aloe Vera Gel to Maintain Table Grape Quality and Safety," J Agric Food Chem (2005), 53:7807-7813.
Machine translation of Spanish Appl. Pub. No. ES 2234431 A1, Jun. 16, 2005, Martinez Romero, et al., (abstract, description, claims) 10 pp.
Machine translation of Abstract only—Japanese Appl. Publ. No. JP 61136583(A), Jun. 24, 1986, Ishii, et al. 1 p.
International Search Report and Written Opinion for PCT/US2016/045850 dated Nov. 18, 2016, 12 pp.
International Search Report and Written Opinion for PCT/US2017/021411 dated Jun. 20, 2017, 14 pp.

(Continued)

*Primary Examiner* — Robert A Wax
*Assistant Examiner* — Thor Nielsen
(74) *Attorney, Agent, or Firm* — Edwin S. Flores; Chalker Flores, LLP

(57) ABSTRACT

The present invention includes compositions and methods for the treatment of plants against pathogens, elimination of insects and to increase the shelf-life of fruits and vegetables that includes coating the plant with undiluted *aloe vera* gel.

16 Claims, 2 Drawing Sheets

(56) References Cited

OTHER PUBLICATIONS

Serrano, Maria et al., "Use of Aloe vera gel coating preserves the functional properties of table grapes," Journal of Agricultural and Food Chemistry, vol. 54, Issue 11, vol. 54, pp. 3882-3886.
Sophia, Ochiki et al., "Effect of Aloe vera gel coating on postharvest quality and shelf life of mango (*Mangifera indica* L.) fruits Var. Ngowe," Journal of Horticulture and Forestry, Jan. 2015, vol. 7, Article No. 13B4D5149545 (pp. 1-7).

* cited by examiner

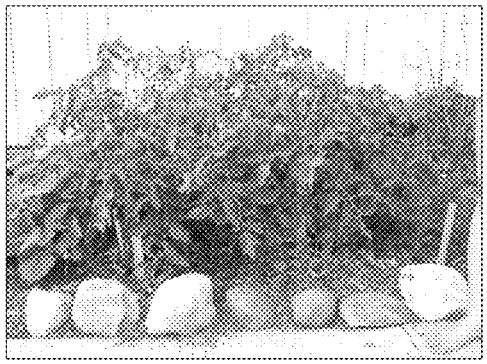
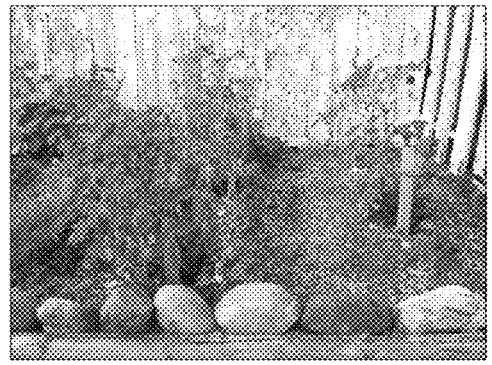
FIG. 1A
FIG. 1B
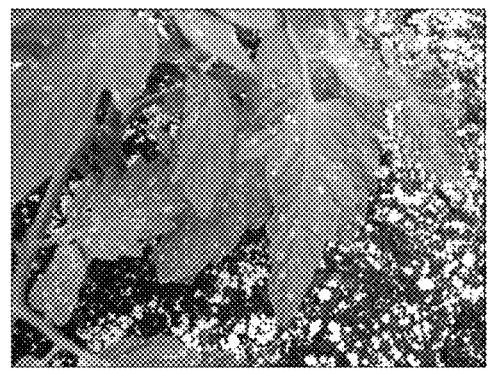
FIG. 2A
FIG. 2B
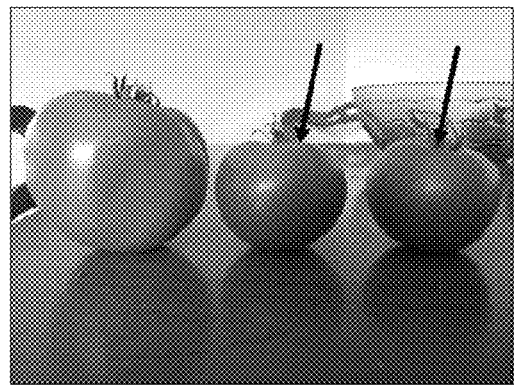
FIG. 3

TREATMENT OF PLANTS, FRUITS AND VEGETABLES TO INCREASE GROWTH, ELIMINATE INSECTS AND INCREASE SHELF-LIFE WITH ALOE VERA GEL

CROSS-REFERENCE TO RELATED APPLICATIONS

This application is a continuation of U.S. patent application Ser. No. 11/941,777, filed on Nov. 16, 2007, which claims priority to U.S. Provisional Application Ser. No. 60/859,336, filed Nov. 16, 2006, the entire contents of which are incorporated herein by reference.

TECHNICAL FIELD OF THE INVENTION

The present invention relates in general to the field of treatments for plants, fruits and vegetables, and more particularly, to compositions and methods for the treatment of plant against plant pathogens, eliminate insects and/or increase the shelf-life of fruits and vegetables.

BACKGROUND OF THE INVENTION

Without limiting the scope of the invention, its background is described in connection with the treatment of plants against pathogens.

In recent years research and development efforts for the treatment of plant pathogens has focused on two main approaches, chemical and genetic. Over the years, more and more powerful chemical agents have been developed and refined to prevent and treat plants. These chemical agents are designed or isolated to affect a critical reproductive step in the growth, maturation or division of the target organism. However, more often than not, the chemical agent has an effect on other plants and animals.

An alternative approach has been to genetically modify the plant itself. For crops this has been a useful technique as the newly modified plants may be introduced in the next crop cycle and monitored. The chemical and genetic have even been used in combination by modifying the plant to resist certain chemicals that the pathogens can not.

Examples of methods for protecting fruits may be found in U.S. Pat. No. 4,946,694, issued to Gunnerson, et al., for a "Liquid coating for fruits." These inventors teach an improved coating for sticky fruits and a process for preparing such coated fruits. More particularly, the coating of the invention comprises a vegetable wax, a vegetable oil, a wetting agent and a protein. The process is said to include the steps of: (a) coating the fruit with a composition that includes a wetting agent and a suspension of a vegetable wax in a vegetable oil, (b) adding to the fruit a composition with a protein, (c) removing excess mixture from the fruit, and (d) drying the fruit. However, the addition of protein greatly increases the cost of the application and provides a potential substrate for attachment.

Yet another chemical coating is taught in U.S. Pat. No. 4,039,470, issued to Kalmar, entitled "Preservative coating for fruits and vegetables." This inventor coats fruits with a finely atomized spray of an acid solution of benzimidazole that must be retained in a separate corrosion resistant chamber prior to being mixed with the wax or resin solution just prior to application.

Yet another coating is taught in U.S. Pat. No. 4,783,342, issued to Polovina and entitled, "Polymeric film coating method for protecting plants, vegetables and fruit from drought," which relates to a method of preserving plants during periods of drought by applying a solid, water permeable film which controls water loss, to the surface of the plants. The same film can also be used to preserve vegetables and fruit. The water permeable film is also effective to preserve cut flowers.

Finally, U.S. Pat. No. 5,922,774, issued to Winslow teaches a method for controlling plant damage by insect herbivores. Briefly, this patent teaches using chemically-synthesized anthraquinones to repelling insect herbivores from plant surfaces and deterring them from feeding on plant surfaces by applying an aqueous dispersion of polycyclic quinone or precursor thereof to the foliage of the plant and/or to the surrounding soil in which the plant is rooted.

Despite the many efforts in this regard, nature finds a way to circumvent and select for those pathogens that are no longer resistant to the chemical or the genetic modification. Furthermore, these methods are most useful for those crops and plants that are replaced seasonally or yearly. Trees, plants and crops that live for many years before replacement, however, are unable to benefit from the genetic manipulation. Furthermore, many, many trees, plants and crops have not been able to be readily manipulated. These plants are still in need of protection and treatment from pathogens without an effect on the local environment, plants and fauna.

SUMMARY OF THE INVENTION

The present invention includes compositions and methods for the treatment of plants using *aloe vera*. It has been found that the present invention is a bio-degradable, non-toxic growth promoter. The *aloe vera* compositions of the present invention repel insects and other pests that affect plant and fruit growth. While hundreds of thousands of tons of pesticides are used by the agricultural and forestry industries every year, the industrial chemicals used are toxic, often non-biodegradable, enter water and food sources and their long-term impact on the environment is, at best unknown and in other cases known to be detrimental. The present invention uses, for the first time, *aloe vera* to treat plants to increase the size and biomass of plants. The treatment method and location include, e.g., the leaves, stalk, roots and as a soil treatment.

The present invention includes compositions and methods for the treatment of plants, fruits and vegetables to increase their shelf-life, repel unwanted parasites. In one embodiment, the present invention includes a method for treating plants by identifying a plant in need of treatment against a pathogen or pest and coating the plant with undiluted untreated gelatinous material from *aloe vera*. The *aloe vera* gel may be a liquid, dry, in gel or other form. The undiluted *aloe vera* may be freeze-dried, heat dried, vacuum dried, air-dried, spray-dried and combinations thereof for use or may be mixed for form a gel or a liquid. In some cases, a stabilizer, an anti-oxidant, a water-repellent, a UV absorbing material and/or an anti-microbial agent (e.g., anti-viral, anti-bacterial, anti-fungal, anti-helminth) may be added to the *aloe* gel. Often the plant will be coated in situ. By plant it is meant herein to include trees (monocots and dicots), plant cells, plant tissue, seeds, seedlings, grafts, fruits, vegetables, sexually or asexually reproducing plants, hybrids, transgenics and the like. In some embodiment, the *aloe* gel may be heated or cooled prior to application, however, it may simply be provided at room or ambient temperature.

The present invention also includes a soil treatment that includes an effective amount of an undiluted *aloe vera* gel adapted for delivery or release into soil to create a treated soil, wherein the plant grown in the treated soil at least 25% larger than a non-treated plant and in some cases from 50 to 100% larger. The plant grown in the treated soil may also be measured by an at least 25% larger fruit or vegetable than a non-treated plant and in some cases from 50 to 100% larger.

The present invention also includes a composition for treating plants that is an undiluted *aloe vera* gel adapted for delivery to one or more plants, fruits or vegetables such that the *aloe vera* coats at least a portion of the plant, fruit or vegetable. The present invention enhances the amount of aloin in the gel. In one embodiment the *aloe vera* is concentrated and may have an aloin content of greater than 1,000 ppm. In another embodiment the *aloe vera* is concentrated and may have an aloin content from 600 ppm to 2,000 ppm. The present invention is obtained by separating the solids and the liquids from *aloe vera*, while concentrating the aloin.

The present invention also includes a method for increasing the growth of a plant by treating the plant with an *aloe vera* gel with aloin, wherein the plant grows at least 25% larger than a non-treated plant. The *aloe vera* may be a liquid, a gel, dry, ground, whole or combinations thereof. The *aloe vera* may be freeze-dried, heat dried, vacuum dried, air-dried, spray-dried and combinations thereof. The method of treatment and the composition may also include adding to the *aloe vera*: a stabilizer, anti-oxidant, a water-repellent, a UV absorbing agent, an anti-microbial agent, or combinations thereof. In one specific embodiment, the plant is coated in situ, in the soil, added as a soil treatment, may be added at the base of the plant, may be sprayed or misted on the leaves of the plant or combinations thereof.

It has also been found the using the present invention the plant, its fruit or vegetable has an increase in the size and number of fruit or vegetable size, fruit or vegetable number and combinations thereof. In one example, the plant is a tree. For large scale use, the *aloe vera* of the present invention may be formulated for aerial spraying. The present invention can be loaded into a bottle or canister that permits for formation of an aerosol, e.g., a canister with the *aloe vera* that may be pressurized or is under pressure for delivery of the payload in droplet form.

BRIEF DESCRIPTION OF THE DRAWINGS

For a more complete understanding of the features and advantages of the present invention, reference is now made to the detailed description of the invention along with the accompanying figures and in which:

FIGS. 1A and 1B shows a whole tomato plant treated with (1A) the *aloe vera* preparation of the present invention or without treatment (1B);

FIG. 2 shows the leaves of a tomato plant treated with (2A) the *aloe vera* preparation of the present invention or without treatment (2B);

FIG. 3 shows the fruits of a tomato plant treated with (left) the *aloe vera* preparation of the present invention or without treatment (middle and right); and FIG. 4 is a graph that compares the number of fruits from a tomato plant treated with the *aloe vera* preparation of the present invention or without treatment.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

*Aloe vera*, a tropical or subtropical plant of the genus *Aloe* has lance shaped leaves which contain a viscous but essentially clear gel which is given structural rigidity by hairlike connective fibers that run through it. The clear gel of the *aloe vera* is to be distinguished from the thick, mucilaginous yellow juice that occurs about the base of the plant leaves and adjacent the rind of the leaf. This juice, known as aloin, has been used for many years as an ingredient in many cathartics and purges. The aloin component of *aloe vera* includes, generally, several anthraquinones. The anthraquinones for use with the present invention may includes those from *aloe*, senna, rhubarb, and Cascara buckthorn), fungi, lichens, and insects.

It is known that the therapeutic qualities of the clear gel of *aloe vera* leaves depend to a large extent on the freshness of the gel. For example, the pain of a jelly fish sting may be stopped not to recur by applying the clear gel from a leaf that has just been cut, but if the gel has been exposed to air and light for about one and a half hours, these powers are greatly diminished if not lost. In some cases, however, relatively old unstabilized gel has been found to be effective and apparently the varying efficacy of a fresh gel for different medicinal purposes reflects the fact that the gel is a complex mixture of substances whose natural stability on exposure to air and light at different temperatures differ from batch to batch.

The raw material for preparing the cold process stabilized *aloe vera* gel is obtained from the leaves of fully mature *aloe vera* plants. For example, four to five year old plants are used to ensure full maturity to obtain a higher quality of leaves containing a larger amount of gel. The plants are grown under controlled conditions so that the size and structure of the leaves are more uniform, enabling accurate measurement and selection of quantities of materials to be used in the purification process.

*Aloe vera* leaves are processed as soon as possible after cutting from the plant. Immediate processing of the *aloe vera* leaves prevents degradative decomposition of the gel material as possible which begins upon cutting due to natural enzymatic reactions as well as growth of bacteria within the gel due to the presence of oxygen. After cutting, the *aloe vera* leaves are washed in water or a water and detergent mixture. The leaves are then washed with a suitable bacteriocide and fungicide. For example, the leaves can be soaked in a water and chlorine solution for about 5 to 10 minutes, rinsed with sterilized water, and dried to limit any lint on the leaves.

The *aloe vera* gel is separated from the leaf by first slicing and grinding the leaves. The most common method of removing the gel from the rind is the hand-fillet method, although semi-automated and automated methods also exist. Any grinder known in the *aloe vera* art can be used. The clear *aloe vera* gel is then ground to form a gel that includes aloin. Often, the gel will include a solid phase or reticle, which is known as the leaf pulp. It has been found that any finisher known in the *aloe vera* art can be used to separate the pure gel from the pulp. Briefly, the ground leaf mixture is fed into the finishing cavity, which is a space created by a spiral with specially designed flights and contained inside are a plurality of 360 degree cylindrical screens having openings on the order of one-quarter of an inch in diameter, to remove the large green pulpy portions, and ending with one having an opening on the order of 0.5 microns in diameter. As the spiral rotates, the more liquid phase of the ground leaf mixture is separated from the solid phase as the liquid phase migrates toward the area outside the screen. Once through the screen, the liquid phase flows into a fully enclosed stainless steel pan. At this point, the *aloe vera* mixture is generally clear yellow color in appearance. The yellow color is due to the presence of the aloin in the *aloe vera* mixture. Once separated from the liquid phase, the solid phase of the ground leaf mixture is discarded. One advantage of the hand-fillet method is the reduction in overall aloin concentration, but not its elimination.

The filter that removes the carbon from the *aloe vera* mixture may be, e.g., a filter press, as is well known in the art of *aloe vera* manufacturing. A typical filter press is cylindrical in shape and the filter press and filters are arranged in a horizontal position. In-line, continuous filtration systems are also applicable to remove unwanted carbon powder. A filtering aid, such as diatomaceous earth, can be added to the *aloe vera* mixture to enhance the filtering ability of the filter press, if so desired. In some embodiments, a diatomaceous earth filter may be used.

Figure 4:
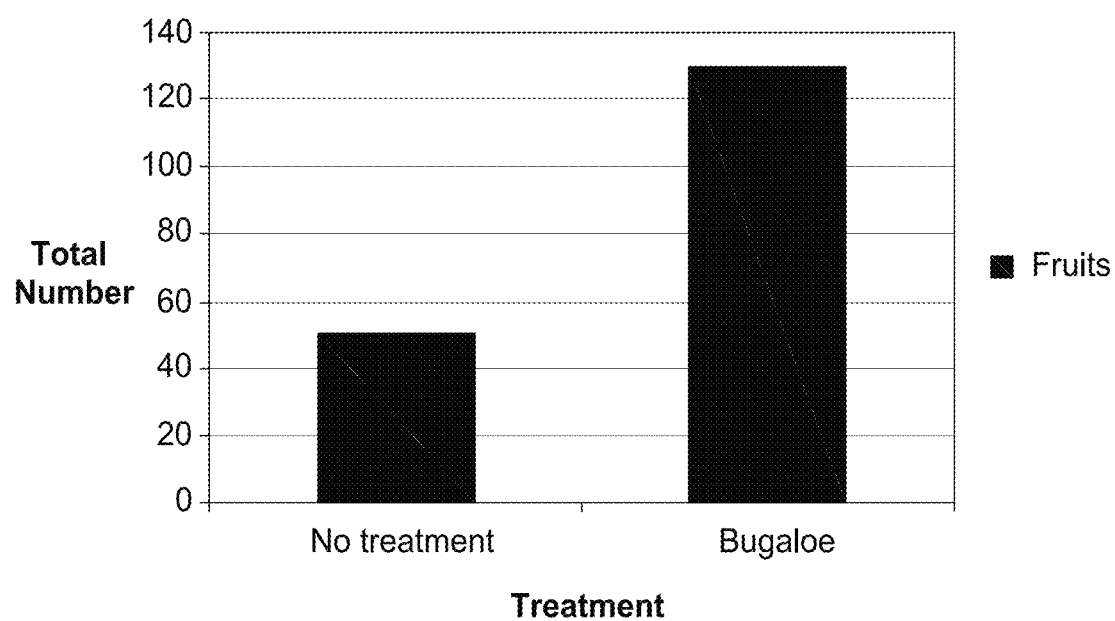

The mixture can be passed through an additional filter system to insure removal of any remaining small amounts of carbon and other unwanted material, if so desired. An example of such a filter system is a series of cartridge filters, ionic filters, size exclusion filters and the like that are capable of removing material from the *aloe vera* mixture down to a size of on the order of 10 microns. The filters used in this step of the process are generally the cartridge type of filters that are commonly used in the pharmaceutical industry. The filters may be densely packed fiber material, a polypropylene or a positively charged polypropylene material.

To the extent necessary, removal of bacteria, fungi and other organisms can be accomplished by using a combination of methods to assure that all bacteria are removed. This can include the use of chemical compounds such as glucose oxidase, boiling, ultraviolet light and the use of bacteria removing filters. In some embodiments, the *aloe* gel may also include additives or preservatives, e.g., sodium benzoate may be added in sufficient quantities to obtain a 0.1% solution of sodium benzoate in the final mixture. Another example of an additive may be a 0.1% solution of glucose oxidase/catalase. After addition of the additives, these may be incorporated into the gel using a mixer or blender and the components are mixed thoroughly for about 10 minutes. The gel is then allowed to sit for approximately 1 hour. To the extent needed, enough citric acid or other acid may added to the gel to adjust the pH to about 3.6.

After treatment in this manner the *aloe vera* composition may be concentrated by lyophilization with liquid nitrogen to a predetermined concentrate volume if desired. It may then be transferred to amber bottles and kept in a cool place for future use. Or, as an alternative, it may be stored without such concentration in plastic-lined barrels.

The following example is set forth for the purpose of illustrating one embodiment of the present invention and is not to be interpreted as a limitation there of or in any limiting fashion.

Example 1. Spraying, Dipping or Washing

The stabilized *aloe vera* gel preparations of the subject invention can be effectively employed to coat fruits and vegetables in situ, e.g., by spraying by hand, spraying mechanically, via aerial spraying, dipping, washing by hand and the like. In this capacity, the ability of the stabilized *aloe vera* gel to fully coat the entire surface of the target fruit or vegetable is especially useful. In one form, it was found that the *aloe vera* gel preparation of the subject invention had enhanced efficacy as well as enhanced ability to remain stable and substantially free of bacteria or fungi for substantial periods of time.

FIGS. 1A and 1B shows a whole tomato plant treated with (1A) the *aloe vera* preparation of the present invention or without treatment (1B). Briefly, *aloe vera* liquid or gel is used to treat the plant. In one method, an effective amount of the *aloe vera* is prayed on the entire plant. In one example, the hand-filleted *aloe vera* gel is dissolved 12 ounces into one gallon of water and sprayed on the plant. As shown in FIG. 1, the plants were almost twice the size.

FIG. 2 shows a close-up of the leaves of a tomato plant treated with (2A) the *aloe vera* preparation of the present invention or without treatment (2B). Again, hand-filleted *aloe vera* gel is dissolved 12 ounces into one gallon of water and sprayed on the leaves of the plant. The *aloe vera* treated plant was without infection, while the leaves of the non-treated plant show little if any attack from parasites.

FIG. 3 shows the fruits of a tomato plant treated with (left) the *aloe vera* preparation of the present invention or without treatment (middle and right). The plants and the fruit was sprayed or misted with a composition adapted for administration on the plant. For example, the *aloe vera* can be added without dilution, but may be diluted to 0.1, 0.5, 1, 2, 5, 8, 10, 12, or 16 ounces of *aloe* in water.

FIG. 4 is a graph that compares the number of fruits from a tomato plant treated with the *aloe vera* preparation of the present invention or without treatment. In combination, FIGS. 3 and 4 demonstrate that the treated tomato plants had an increase in both the number of fruits but also their size. It is believed, but in no way a limitation, that the reduced stress on the plant from plant parasites leads to an increase focus on plant growth and fruit production.

Example 2. Continuous Flow

In operation, a vat or source of pure *aloe vera* gel is pumped through one or more nozzles over a bed or target fruits or vegetables. For a continuous coating or spraying operation it is often convenient to provide the fruit or vegetable into a coating or spraying location or chamber on a conveyor system. For recovery and recycling of the *aloe* gel, a mesh may be used that permits the *aloe* gel to traverse the coating location and enter a capture tank or vessel for recycling. The *aloe* gel to coat the fruits or vegetables may be in liquid or powder form when sprayed.

In another form of continuous coating, the fruits or vegetables may be provided by a linear conveyor system, a rotating system, a batch system or combinations thereof. For use with any of these systems the pure *aloe* gel may be in a liquid form, e.g., chilled, at room temperature or at an elevated temperature and the fruits and/or vegetables are exposed to the pure, undiluted *aloe* gel for 0.5, 1, 10, 15, 20, 30, 45 or 60 seconds. For other embodiments, the fruits and/or vegetables are exposed to the pure, undiluted *aloe* gel for 0.5, 1, 10, 15, 20, 30, 45 or 60 minutes. Most often, the pure *aloe vera* gel will be recycled and replenished as needed based on the application, cleanliness of the fruits or vegetables, temperature, operating conditions, length of exposure to the fruits or vegetables and the like.

Example 3. In Situ Treatment of Plants

During growth and when there is the potential exposure to plant pathogens, plants may be treated by any number of methods with the undiluted *aloe* gel. Often, the plant is expected to continue to live and the plant must be treated in situ, e.g., outdoors or indoors. For outdoor treatment, and depending on the local environmental circumstances it will often be important to treat the plants such that repeated exposure to water will not cause the effect of the *aloe* gel to diminish immediately. As such, any number of water-repellents may be used in conjunction with the present invention. One such repellent may be wax that is included with the *aloe* gel at a temperature at which it is liquid but then solidifies upon a decrease in temperature, upon exposure to oxygen and the like. The water-repellent application will be particularly useful for the treatment of plants, e.g., plants with fruits and vegetables, which are outdoors. Using the present invention, it is possible to treat entire plants, such as trees and even forests to ameliorate the effects of a particular fungus, bacteria, virus or other blight.

The present invention may also be used to treat plant cells, plant tissues, seeds, seedlings, and the like, in situ, in vivo, in vitro and the like. In fact, these plant cells may even be stored in the *aloe vera*. It has been found that coating fruits and vegetables, before, during and/or after they have been picked significantly increases the shelf-life of the fruits or vegetables.

In fact, the present invention may be used in conjunction with anti-microbial agents that have an additive or a synergistic effect on the affected plant or area. One distinct advantage of the present invention is that pure *aloe* gel is completely non-toxic to humans, pets and animals. When provided in a powder form, semi-powder form, as a gel or as a pure *aloe* gel droplet over an extended area, e.g., a forest or portion thereof, a line of prevention may be created to prevent and protect entire areas with limited spraying. For example, the pure *aloe* gel of the present invention may be used with conventional aerial-spraying equipment and planes to deliver on crops, forest, regions and the like.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

In the claims, all transitional phrases such as "comprising," "including," "carrying," "having," "containing," "involving," and the like are to be understood to be open-ended, i.e., to mean including but not limited to. Only the transitional phrases "consisting of" and "consisting essentially of," respectively, shall be closed or semi-closed transitional phrases.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for repelling insects, consisting essentially of:
    identifying a plant in need of repelling insects and enhanced plant growth; and
    placing on the plant an effective amount of an isolated and stabilized gel obtained from an *aloe vera* plant and enhanced with additional aloin in an amount sufficient to repel insects and to enhance growth of the plant by at least 25% more than a non-treated plant, wherein the aloin-enhanced *aloe vera* gel repels insects from an area where insects are not desired, wherein the aloin enhancement is at least 600, 800, 1,000 or 2,000 ppm.

2. The method of claim 1, wherein the *aloe vera* gel is dried, ground, whole or concentrated.

3. The method of claim 1, wherein the *aloe vera* gel is sprayed on a plant, is placed on the soil at or about the plant, is integrated into the soil of a plant, or combinations thereof.

4. The method of claim 1, wherein the *aloe vera* gel is freeze-dried, heat dried, vacuum dried, air-dried, spray-dried and combinations thereof.

5. The method of claim 1, further comprising adding to the gel: a stabilizer, anti-oxidant, a water-repellent, a UV absorbing agent, an anti-microbial agent, or combinations thereof.

6. The method of claim 1, wherein the plant is coated in situ.

7. The method of claim 1, further comprising the step of heating the *aloe* gel prior to application.

8. The method of claim 1, wherein the plant comprises a fruit or vegetable.

9. A method for repelling insects, consisting essentially of:
    identifying a plant in need of repelling insects and enhanced plant growth; and
    placing on the plant an effective amount of an isolated and stabilized gel obtained from an *aloe vera* plant and enhanced with additional aloin in an amount sufficient to repel insects and to enhance growth of the plant by at least 25% more than a non-treated plant, wherein the aloin-enhanced *aloe vera* gel repels insects from an area where insects are not desired.

10. The method of claim 9, wherein the *aloe vera* gel is dried, ground, whole or concentrated.

11. The method of claim 9, wherein the *aloe vera* gel is sprayed on a plant, is placed on the soil at or about the plant, is integrated into the soil of a plant, or combinations thereof.

12. The method of claim 9, wherein the *aloe vera* gel is freeze-dried, heat dried, vacuum dried, air-dried, spray-dried and combinations thereof.

13. The method of claim 9, further comprising adding to the gel: a stabilizer, anti-oxidant, a water-repellent, a UV absorbing agent, an anti-microbial agent, or combinations thereof.

14. The method of claim 9, wherein the plant is coated in situ.

15. The method of claim 9, further comprising the step of heating the *aloe* gel prior to application.

16. The method of claim 9, wherein the plant comprises a fruit or vegetable.

* * * * *